United States Patent [19]

Inoue et al.

[11] Patent Number: 4,939,260

[45] Date of Patent: Jul. 3, 1990

[54] PROCESS FOR PRODUCING AROMATIC NITRILES OR HETEROCYCLIC NITRILES

[75] Inventors: Akira Inoue, Hirakata; Mitsuaki Ikeda, Himeji; Kunio Sano, Ako; Sadao Terui; Toshihide Kanzaki, both of Hyogo, all of Japan

[73] Assignee: Nippon Shokubai Kagaku Kogyo Co., Ltd., Osaka, Japan

[21] Appl. No.: 193,084

[22] Filed: May 12, 1988

[30] Foreign Application Priority Data

May 12, 1987 [JP] Japan .................................. 62-113462

[51] Int. Cl.$^5$ .................. C07D 213/57; C07D 213/84; C07C 255/50; C07C 255/52
[52] U.S. Cl. ..................................... 546/286; 546/287; 558/327
[58] Field of Search .................. 558/327; 546/286, 287

[56] References Cited

U.S. PATENT DOCUMENTS

| 3,959,297 | 5/1976 | Ishioka et al. | 546/286 |
| 4,482,719 | 9/1984 | Helmut et al. | 546/286 |

FOREIGN PATENT DOCUMENTS

| 2427191 | 1/1975 | Fed. Rep. of Germany | 558/327 |
| 0013611 | 7/1966 | Japan | 558/327 |
| 1065444 | 4/1967 | United Kingdom | 558/327 |
| 1124457 | 8/1968 | United Kingdom | 558/327 |
| 1280326 | 7/1972 | United Kingdom | 558/421 |

*Primary Examiner*—Alan L. Rotman
*Attorney, Agent, or Firm*—Sherman and Shalloway

[57] ABSTRACT

A process for producing aromatic or heterocyclic nitriles, which comprises reacting an alkyl-substituted aromatic hydrocarbon or an alkyl-substituted heterocyclic compound with ammonia and oxygen in the presence of a catalyst composition comprising (a) at least one composite oxide selected from the group consisting of a binary composite oxide comprising titanium and silicon, a binary composite oxide comprising titanium and zirconium and a ternary composite oxide comprising titanium, silicon and zirconium, and (b) an oxide of at least one metal selected from the group consisting of vanadium, molybdenum, tungsten, chromium, antimony, bismuth, phosphorus, niobium, iron, nickel, cobalt, manganese and copper.

19 Claims, No Drawings

PROCESS FOR PRODUCING AROMATIC NITRILES OR HETEROCYCLIC NITRILES

This invention relates to a process for producing nitriles by reacting alkyl-substituted aromatic hydrocarbons or alkyl-substituted heterocyclic compounds with ammonia and oxygen.

It has previously been proposed to use such elements as antimony, vanadium, chromium, molybdenum, tungsten and manganese as catalysts for the production of aromatic nitriles by ammoxidation of alkyl-substituted hydrocarbons. They have been used as oxides, in many cases as mixtures and sometimes as compounds, mostly on carriers such as silicon dioxide or aluminum oxide. Few of these catalysts permit high space time yields and simultaneously have good selectivity. They give rise to other industrial problems. For example, they may require a considerably stoichiometrically excessive amount of ammonia, or temperature control of layers of these catalysts is difficult. Furthermore, they have a short active lifetime and cannot maintain production stably over long periods of time.

It is an object of this invention to remedy these defects of the prior art.

The present inventors made extensive investigations in order to achieve this object, and have found that these problems can all be solved by using a catalyst composition comprising (a) at least one composite oxide selected from the group consisting of a binary composite oxide comprising titanium and silicon, a binary composite oxide comprising titanium and zirconium and a ternary composite oxide comprising titanium, silicon and zirconium, and (b) an oxide of at least one metal selected from the group consisting of vanadium, molybdenum, tungsten, chromium, antimony, bismuth, phosphorus, niobium, iron, nickel, cobalt, manganese and copper.

Thus, according to this invention there is provided a process for producing aromatic or heterocyclic nitriles, which comprises reacting an alkyl-substituted aromatic hydrocarbon or an alkyl-substituted heterocyclic compound with ammonia and oxygen in the presence of the above catalyst composition.

The characteristic feature of the catalyst used in this invention is that it uses as component (a) at least one composite oxide selected from the group consisting of a binary composite oxide comprising titanium and silicon (to be referred to as $TiO_2$—$SiO_2$), a binary composite oxide comprising titanium and zirconium (to be referred to as $TiO_2$—$ZrO_2$), and a ternary composite oxide comprising titanium, silicon and zirconium (to be referred to as $TiO_2$—$SiO_2$—$ZrO_2$).

Generally, a binary composite oxide of titanium and silicon is known as solid acids, and shows a marked acidity not seen in the individual oxides constituting it, and has a high surface area.

$TiO_2$—$SiO_2$ is not a mere mixture of titanium oxide and silicon oxide, and is considered to exhibit its unique properties as a result of formation of a so-called binary composite oxide from titanium and silicon. Furthermore, a binary composite oxide of titanium and zirconium and a ternary composite oxide of titanium, zirconium and silicon can also be defined as composite oxides having the same properties as $TiO_2$—$SiO_2$.

X-ray diffractometry shows that the above composite oxides have a microstructure which is amorphous or nearly amorphous.

Previously, substances of a low surface area, for example, aluminum oxide, titanium oxide calcined at about 1000° C., alpha-alumina or anatase (see British Patent No. 1280326, U.S. Pat. No. 4,065,487, British Patent No. 1476745 and U.S. Pat. No. 3,959,297) have been used as carriers for ammoxidation catalysts for alkyl-substituted hydrocarbons, and catalysts having a high surface area have not been known to be used for this purpose. This was because it was thought that on a catalyst at a high temperature in an oxidizing atmosphere, the alkyl-substituted aromatic compound and the ammonia added undergoes decomposition, and the selectivity of the catalyst is very much reduced. As a result of long-term research work on solid acids, the present inventors found that catalyst comprising composite oxides are suitable for ammoxidation in spite of their high surface area.

It is considered that since the composite oxides have the property of effectively adsorbing ammonia, they play a role of converting alkyl-substituted aromatic hydrocarbons into nitriles with good selectivity by adding ammonia required for ammoxidation in a small amount close to the stoichiometric amount. Production of nitriles by using a small amount of ammonia is economically advantageous because the cost that goes into ammonia can be curtailed. Furthermore, because the amount of ammonium carbonate formed as a by-product from carbon dioxide and ammonia is reduced, it is also advantageous to the collection and purification of nitriles, or other operations in the production process.

The composite oxide components (a) constituting the catalyst composition used in this invention, i.e. $TiO_2$—$SiO_2$, $TiO_2$—$ZrO_2$ and $TiO_2$—$SiO_2$—$ZrO_2$ preferably have a surface area of at least 30 $m^2/g$, more preferably at least 70 $m^2/g$. As the specific surface area of the composite oxide (a) is higher, ammonia acts more effectively in the action of forming nitriles.

The composition of the composite oxide (a) is preferably such that when calculated as oxides, the proportion of $TiO_2$ is 20 to 95 mole % and the proportion of $SiO_2$ or $ZrO_2$ or the sum of $SiO_2$ and $ZrO_2$ is 5 to 80 mole % (provided that the total proportion of $TiO_2$+$ZrO_2$+$SiO_2$=100 mole %).

The catalyst component (b) used in the catalyst composition in this invention is an oxide of at least one metal selected from the group consisting of vanadium, molybdenum, tungsten, chromium, antimony, bismuth, phosphorus, niobium, iron, nickel, cobalt, manganese and copper. As required, an oxide of an alkali metal may be used in combination. The oxide of at least one metal selected from the above group may include a composite oxide of at least two metals selected from the above group, for example $V_2O_5$—$Sb_2O_3$. The catalyst component (b) may be properly selected depending upon the type of the starting material. Those which contain vanadium or tungsten are preferred. Especially preferred are those containing both vanadium and antimony.

In preparing the catalyst composition in this invention, the catalyst component (b) should be added after the composite oxide as catalyst component (a) has been calcined. If a large amount of a precursor (such as a V compound) of the catalyst component (b) exists before the calcination of the component (a), it adversely affects the properties of the finished catalyst, and the desired catalyst performance cannot be obtained. For example, U.S. Pat. No. 3,959,297 discloses a process for producing 3-cyanopyridine which comprises ammoxidation of 2-methyl-5-ethylpyridine using a large excess of ammonia in the presence of a V-Ti-Zr three-component metal oxide obtained by calcining a coprecipitate of the individual catalyst components. The present inventors repeated this process and found that the catalyst composition of the U.S. Patent has a specific surface area of as low as about 10 m²/g, and under such reaction conditions that the mole ratio of ammmonia to an alkyl-substituted aromatic hydrocarbon in the feed gas is lowered, the corresponding aromatic nitrile is difficult to obtain in a high yield (see Comparative Example 2 given hereinafter).

The catalyst composition used in this invention is composed usually of 50 to 99% by weight of the catalyst component (a) and 50 to 1% by weight of the catalyst component (b), and preferably of 70 to 95% by weight of the catalyst component (a) and 30 to 5% by weight of the catalyst component (b) with the catalyst component (b) being composed of 2 to 5% by weight of an oxide of vanadium as $V_2O_5$ and 5 to 15% by weight of an oxide of antimony as $Sb_2O_3$.

To support the catalyst composition of this invention on an inert carrier produces a favorable result. The inert carrier preferably has a specific surface area of 0.05 to 10 m²/g. Examples of the inert carrier include alumina, silica, silica-alumina, silicon carbide, bentonite, diatomaceous earth, titania, zirconia, magnesia, cordierite, mullite, pumice and inorganic fibers.

In the preparation of $TiO_2$—$SiO_2$ used in this invention, sources of titanium may be selected from inorganic titanium compounds such as titanium chloride and titanium sulfate and organic titanium compounds such as titanium oxalate and tetraisopropyl titanate. Sources of silicon may be selected from inorganic silicon compounds such as colloidal silica, water glass (sodium silicate) and silicon tetrachloride and organic silicon compounds such as tetraethyl silicate. These raw materials may contain minor amounts of impurities and inclusions, but they pose no problem unless they greatly affect the properties of the resulting $TiO_2$—$SiO_2$.

Examples of preferred methods of preparing $TiO_2$—$SiO_2$ are given below.

(1) A method which comprises mixing titanium tetrachloride with silica sol, adding ammonia to the mixture to form a precipitate, washing the precipitate, drying it and then calcining the dried product at 300° to 800° C.

(2) A method which comprises adding an aqueous solution of sodium silicate to titanium tetrachloride, reacting them to form a precipitate, washing the precipitate, dryng it, and calcining the dried product at 300° to 800° C.

(3) A method which comprises adding ethyl silicate, $(C_2H_5O)_4Si$, to a water-alcohol solution of titanium tetrachloride to perform hydrolysis and form a precipitate, washing the precipitate, drying it, and calcining the dried product at 300° to 800° C.

(4) A method which comprises adding ammonia to water-alcohol solution of titanium oxide chloride (TiOCl₂) and ethyl silicate to form a precipitate, washing the precipitate, drying it, and calcining the dried product at 300° to 800° C.

Of these, the method (1) is especially preferred. This method is carried out more specifically by the following procedure. A titanium source compound and a silicon source compound are taken so as to provide a predetermined mole ratio of $TiO_2$ and $SiO_2$. They are mixed to form an acidic aqueous solution or a sol in which the concentrations of titanium and silicon, calculated as oxides, are 1 to 100 g/liter. The solution or sol is maintained at 10° to 100° C., and aqueous ammonia as a neutralization agent is added dropwise to it with stirring, and the mixture is maintained at a pH of 2 to 10 for 10 minutes to 3 hours to form a co-precipitated compound of titanium and silicon. The compound was separated by filtration, well washed, and dried at 80° to 140° C. for 1 to 10 hours. The dried product is calcined ( at 300° to 800° C. for 1 to 10 hours to give $TiO_2$—$SiO_2$.

$TiO_2$—$ZrO_2$—$SiO_2$ may be prepared by the same method as in the preparation of $TiO_2$—$SiO_2$. Sources of zirconium may be selected from inorganic zirconium compounds such as zirconium chloride and zirconium sulfate and organic zirconium compound such as zirconium oxalate. $TiO_2$—$ZrO_2$—$SiO_2$ can be easily prepared by using the zirconium compound together with the titanium compound in the method described above.

$TiO_2$—$ZrO_2$ may be prepared in a similar manner.

The catalyst composition may be obtained by using $TiO_2$—$SiO_2$, $TiO_2$—$ZrO_2$ and $TiO_2$—$SiO_2$—$ZrO_2$ prepared by the above methods. For example, an aqueous solution of a precursor (such as a metal salt) of the catalyst component (b) and a molding aid are added to a powder of $TiO_2$—$SiO_2$ and they are mixed and kneaded while adding a moderate amount of water. The mixture is molded by an extruder into a desired shape such as a pellet or honeycomb. The molded product is dried at 50° to 120° C., and then calcined in air at 300° to 800° C., preferably 400° to 600° C. for 1 to 10 hours, preferably 2 to 6 hours, to give a finished catalyst composition.

On the other hand, the catalyst composition supported on the inert carrier may be prepared by, for example depositing a slurry containing $TiO_2$—$SiO_2$ and a precursor of the catalyst component (b) on granular silicon carbide by a baking method. The amount of the catalyst components deposited may vary depending upon the carrier used, the composition of the catalyst, etc. Usually, it is at least 3 % by weight, preferably at least 7 % by weight.

The precursor of the catalyst component (b) may be selected, for example, from nitrates, sulfates, chlorides and hydroxides of the above-specified metals.

The preparation of the catalyst composition used in this invention is, of course, not limited to the methods specifically described above.

The shape of the catalyst composition may be selected, for example, from a pellet, a honeycomb, a solid cylinder, a hollow cylinder, a plate, a ribbon, a corrugated board, a pipe, a doughnut and a lattice.

The catalyst composition according to this invention is suitable for use in a fixed bed or in a fluidized bed.

The reaction of obtaining a nitrile by reacting an alkyl-substituted aromatic hydrocarbon or an alkyl-substituted heterocyclic compound with ammonia and oxygen in the presence of the catalyst composition prepared as above is usually carried out in the gaseous phase. The reaction is carried out mainly under atmospheric pressure or a slightly elevated pressure of up to 3 atmospheres, at a temperature of 180° to 600° C., especially 250° to 500° C. The mole ratio of molecular oxygen to the alkyl-substituted aromatic hydrocarbon or the alkyl-substituted heterocyclic compound in the feed gas is at least 2.0, preferably 2.5 to 30. The mole ratio of ammonia to the alkyl-substituted aromatic hydrocarbon or the alkyl-substituted heterocyclic compound in the feed gas is at least 1.5, preferably 2.0 to 20. As required, the gaseous starting mixture may be used after it is diluted with an inert gas such as nitrogen or steam. Air is conveniently used as the molecular oxygen-containing gas.

Good results are obtained by contacting the feed starting gas with the catalyst composition at a space velocity (calculated for NTP) of 300 to 5,000 hr$^{-1}$, preferably 400 to 3,000 hr$^{-1}$. The unreacted alkyl-substituted aromatic hydrocarbon or alkyl-substituted heterocyclic compound and ammonia may be recycled for re-use.

The alkyl-substituted aromatic hydrocarbon and the alkyl-substituted heterocyclic compound may generally be those in which the alkyl group at the side chain has not more than 3 carbon atoms. Typical examples include alpha-, beta- or gamma-picoline, 2-methyl-5-ethylpyridine, toluene, ethylbenzene, n-propylbenzene, cumene, o-, m- or p-xylene, o-, m- or p-ethyltoluene, o-, m- or p-isopropyltoluene, o- m- or p-diethylbenzene, o-, m- or p-diisopropylbenzene, mesitylene, alpha- or beta-methylnaphthalene.-, dimethylnaphthalene and mono- or di-methylanthracene. Aromatic compounds resulting from replacing hydrogens of the aromatic ring of these compounds by groups which do not participate in the reaction, such as fluorine, chlorine, bromine, a nitrile group or a methoxy group, such as o-, m- or p-chlorotoluene, o- m- or p-methylanisole, o-, m- or p-tolunitrile or dichlorotoluene may be cited as another group of examples.

Usually, air is used as the oxygen-containing gas. There may also be used oxygen, a mixture of oxygen and air, a mixture of air and carbon dioxide, a mixture of air and steam and a mixture of air and nitrogen.

According to the process of this invention, there can be formed picolinonitrile from alpha-picoline; nicotinonitrile from beta-picoline; isonicotinonitrile from gamma-picoline; 2,5-dicyanopyridine and nicotinonitrile from 2-methyl-5-ethylpyridine; chlorobenzonitrile from chlorotoluene; cyanoanisole from methylanisole; phthalonitrile from tolunitrile; and dichlorobenzonitrile from dichlorotoluene. Furthermore, there can be obtained benzonitrile from toluene, ethylbenzene, n-propylbenzene or cumene; o-tolunitrile, phthalonitrile and phthalimide from o-xylene, o-isopropyltoluene, o-diethylbenzene or o-diisopropylbenzene; m-tolunitrile and isophthalonitrile from m-xylene, m-isopropyltoluene, m-diethylbenzene or m-diisopropylbenzene; p-tolunitrile and terephthalonitrile from p-xylene, p-isopropyltoluene, p-diethylbenzene or p-diisopropylbenzene; tricyanobenzene, dicyanomonomethylbenzene and monocyanodimethylbenzene from mesitylene; and cyanonaphthalene and phthalonitrile from methylnaphthalene.

The following examples illustrate the present invention in greater detail. It should be understood that the invention is not limited to these examples.

EXAMPLE 1

A composite oxide (a) of titanium and silicon was prepared by the following method.

An aqueous sulfuric acid solution of titanyl sulfate containing 200 g/liter of TiOSO$_4$ (as TiO$_2$) and 1100 g/liter (total) of H$_2$SO$_4$ was used as a titanium source. Separately, 280 liters of aqueous ammonia (25% NH$_3$) was added to 400 liters of water, and 16.9 kg of Snowtex NCS-30 (silicasol made by Nissan Chemical Co., Ltd.; about 30% by weight as SiO$_2$) was added. An aqueous sulfuric acid solution containing titanium obtained by diluting the 153 liters of the above aqueous sulfuric acid solution of titanyl sulfate to 300 liters of water was gradually added dropwise with stirring to form a coprecipitated gel. After standing for 15 hours, the resulting gel of TiO$_2$—SiO$_2$ was filtered, washed with water and then dried at 200° C. for 10 hours.

The dried product was calcined in air at 550° C. for 6 hours to give a powder having a TiO$_2$/SiO$_2$ mole ratio of 85:15 and a BET specific surface area of 180 m$^2$/g. The resulting powder will be designated as TS-1. Using this powder, a catalyst composition was prepared by the following procedure.

Ammonium metavanadate (NH$_4$VO$_3$; 23.4 g) was dissolved in an aqueous solution of oxalic acid to prepare an aqueous solution of vanadyl oxalate. Separately, 51.0 g of antimony trioxide (Sb$_2$O$_3$) was dissolved in an aqueous solution of tartaric acid to prepare an aqueous solution of antimony tartarate. The two aqueous solutions were mixed, and 400 g of TS-1 was added. They were well mixed to form a slurry. The slurry was sprayed onto 2 liters of preheated spherical particles of SiC having a diameter of about 5 mm at a deposition rate of 10%, and then calcined at 550° C. for 5 hours under an air current.

Two liters of the catalyst composition so obtained was filled in a stainless steel reaction tube having an inside diameter of 25 mm and heated with a molten salt. A gaseous mixture composed of 3% by volume of toluene, 6% by volume of ammonia, 10% by volume of oxygen and 81% by volume of nitrogen was passed through the reaction tube and reacted at a reaction temperature of 390° C. and a space velocity (for NTP) of 900 hr$^{-1}$. The results of the reaction were as follows:

Conversion of toluene: 98.8 mole %
Yield of benzonitrile: 87.7 mole %
Selectivity for benzonitrile: 88.8 mole %

COMPARATIVE EXAMPLE 1

A catalyst composition was prepared in the same way as in Example 1 except that TiO$_2$ (anatase) having a surface area of 21 m$^2$/g was used instead of the composite oxide (a) having a TiO$_2$/SiO$_2$ mole ratio of 85:15. Using the resulting catalyst, the same reaction as in Example 1 was carried out. The results of the reaction were as follows:

Conversion of toluene: 97.5 mole %
Yield of benzonitrile: 81.7 mole %
Selectivity for benzonitrile: 83.8 mole %

EXAMPLE 2

TiO$_2$—ZrO$_2$ was prepared by the following procedure.

Zirconium oxychloride (ZrOCl$_2$.8H$_2$O; 13.6 kg) was dissolved in 1 m$^3$ of water, and the solution was well mixed with 78 liters of an aqueous sulfuric acid solution of titanyl sulfate having the same composition as in Example 1. After the mixture was well stirred at a temperature of about 30° C., aqueous ammonia was gradually added dropwise until the pH of the mixture reached 7. The mixture was then allowed to stand for 15 hours.

The resulting gel of TiO$_2$—ZrO$_2$ was filtered, washed with water and dried at 200° C. for 10 hours. The dried product was then calcined in an atmosphere of air at 550° C. for 6 hours. The resulting powder had a TiO$_2$/ZrO$_2$ mole ratio of 85:15 and a BET surface area of 130 m$^2$/g. The resulting powder will be designated as TZ-1.

Using TZ-1, a catalyst composition was prepared as in Example 1. Using the resulting catalyst composition, the same reaction as in Example 1 was carried out at a reaction temperature of 430° C. The results of the reaction were as follows:
Conversion of toluene: 95.0 mole %
Yield of benzonitrile: 83.6 mole %
Selectivity for benzonitrile: 88.0 mole %
The BET surface area of the metal oxides in this catalyst excepting the carrier (SiC) was 105 m²/g.

COMPARATIVE EXAMPLE 2

(See U.S. Pat. No. 3,959,297.)

(a) Vanadium pentoxide (182 g) was added to an aqueous solution of oxalic acid and dissolved by heating.

(b) 600 ml of 28% aqueous ammonia was added to an aqueous solution containing 380 g of titanium tetrachloride to form a gel-like precipitate of titanium hydroxide. The precipitate was washed with deionized water, and then filtered by means of suction. The wet gel was added to an aqueous solution of oxalic acid and dissolved by heating.

(c) Zirconyl nitrate (267 g) was dissolved in deionized water.

These three solutions were mixed to form a mixture having a V:Ti:Zr atomic ratio of 1:1:0.5. The mixture was impregnated in 3000 g of SiC having a particle diameter of 5 mm, followed by evaporation to dryness. The dried product was calcined under an air current at 550° C. for 4 hours.

The same reaction as in Example 2 was carried out except that the catalyst composition formed as above was used. At a reaction temperature of 430° C., the conversion of toluene was 84 mole %, the yield of benzonitrile was 49 mole %, and the selectivity for benzonitrile was 58 mole %. The BET surface area of the metal oxides in this catalyst excepting the carrier (SiC) was 11 m²/g.

EXAMPLE 3

TiO$_2$—SiO$_2$—ZrO$_2$ was prepared substantially in accordance with the procedures of Examples 1 and 2. The resulting powder had a TiO$_2$:SiO$_2$:ZrO$_2$ mole ratio of 80:16:4 and a BET surface area of 180 m²/g. The resulting powder will be referred to as TSZ-1.

A catalyst composition was prepared as in Example 1 using this powder. The same reaction as in Example 1 was carried out except that the catalyst composition prepared above was used and the reaction was carried out at a reaction temperature of 400° C. The results of the reaction were as follows:
Conversion of toluene: 98.5 mole %
Yield of benzonitrile: 89.1 mole %
Selectivity for benzonitrile: 90.5 mole %

EXAMPLE 4

Each of the starting compounds indicated below was subjected to ammoxidation in the presence of the catalyst composition prepared by the method of Example 1 under the conditions indicated below. The results are tabulated below.

| Starting compound | Concentration of the starting compound (vol. %) | Mole ratio of NH$_3$/ starting compound | Mole ratio of O$_2$/ starting compound | Contact time (sec.) | Reaction temperature (°C.) | Yield of the desired substance (mole %) |
|---|---|---|---|---|---|---|
| alpha-Picoline | 1.5 | 5.0 | 12.7 | 2.4 | 340 | 73 |
| beta-Picoline | 1.5 | 2.2 | 13.3 | 2.4 | 375 | 85 |
| gamma-Picoline | 1.5 | 2.2 | 13.3 | 2.4 | 300 | 97 |
| p-Methylanisole | 1.5 | 5.0 | 12.7 | 2.4 | 370 | 50 |
| p-Chlorotoluene | 3.0 | 2.0 | 3.3 | 4.3 | 390 | 86 |

EXAMPLE 5

The catalyst composition prepared in Example 1 was tested for life.

The catalyst composition was packed to a height of 4 meters in a tube having an inside diameter of 25 mm and a length of 5 meters and immersed in a molten salt bath, and maintained at 390° C.

A gaseous mixture composed of 3% by volume of toluene, 6% by volume of ammonia, 10% by volume of oxygen and 81% by volume of nitrogen was fed from the upper part of the reaction tube and reacted for 6 months at a space velocity (for NTP) of 900 hr$^{-1}$. Just after the six month period, the yield of benzonitrile was 87.3 mole % which was nearly identical with that obtained in the initial stage.

EXAMPLE 6

Various catalyst compositions were prepared as in Example 1 except that catalyst component (b) of various compositions as shown below was used. Using the resulting catalysts, toluene was subjected to ammoxidation. The results are shown in the following table. In the table, Tol stands for toluene, and BN, for benzonitrile.

| Atomic ratio of component (b) | Tol concentration (vol. %) | NH$_3$/Tol mole ratio | O$_2$/Tol mole ratio | Contact time (sec.) | Reaction temperature (°C.) | Yield of BN (mole %) |
|---|---|---|---|---|---|---|
| V:Cr = 1:0.5 | 1 | 3 | 20 | 5 | 420 | 83 |
| V:Sb:Cr = 1:1.75:0.5 | 3 | 6 | 3 | 4.2 | 400 | 88 |
| V:Sb:Cr:Bi = 5:8:1:2.5 | 1 | 3 | 20 | 2.4 | 390 | 87 |
| V:P:Nb:K = 40:5:2.5:1 | 1 | 3 | 20 | 2.4 | 400 | 79 |
| V:W:Mn = 3:2.3:1 | 1 | 5 | 20 | 5 | 380 | 85 |

What we claim is:

1. A process for producing aromatic or heterocyclic nitriles, which comprises reacting an alkyl-substituted aromatic compound or an alkyl-substituted heterocyclic compound selected from the group consisting of C$_1$-C$_3$ alkyl-substituted benzenes C$_1$-C$_3$ alkyl-substituted naphthalenes and $C_1$–$C_3$ alkyl-substituted pyridines which each may be further substituted by a halogen, nitrile or alkoxy with ammonia and oxygen, in the gas phase, in the presence of a catalyst composition consisting of (a) at least one composite oxide selected from the group consisting of a binary composite oxide consisting of titanium and silicon, a binary composite oxide consisting of titanium and zirconium and a ternary composite oxide consisting of titanium, silicon and zirconium, and (b) an oxide of at least one metal selected from the group consisting of vanadium, molybdenum, tungsten, chromium, antimony, bismuth, phosphorous, niobium, iron, nickel, cobalt, manganese and copper;

wherein said reaction is carried out at a temperature of 180° to 600° C., under a pressure of 1 to 3 atmospheres;

wherein the concentration of said alkyl-substituted aromatic compound or alkyl-substituted heterocyclic compound in the feed gas is 0.5 to 4% by volume, the mole ratio of oxygen to the alkyl-substituted aromatic compound or alkyl-substituted heterocyclic compound in the feed gas is at least 2 and the mole ratio of ammonia to the alkyl-substituted aromatic compound or alkyl-substituted heterocyclic compound in the feed gas is at least 1.5; and wherein the feed gas is fed at a space velocity of 400 to 3000 hr$^{-1}$, for NTP.

2. The process of claim 1 wherein the reaction temperature is 250° to 500° C.

3. The process of claim 1 wherein the mole ratio of oxygen to the alkyl-substituted aromatic compound or alkyl-substituted heterocyclic compound in the feed gas is from 2.5 to 30.

4. The process of claim 1 wherein the mole ratio of ammonia to the alkyl-substituted aromatic compound or alkyl-substituted heterocyclic compound in the feed gas is from 2 to 20.

5. The process of claim 1 wherein the alkyl-substituted aromatic compound is toluene.

6. The process of claim 1 wherein the alkyl-substituted aromatic compound is methyl anisole.

7. The process of claim 1 wherein the alkyl-substituted heterocyclic compound is alpha-picoline, beta-picoline or gamma-picoline.

8. The process of claim 1 wherein the alkyl-substituted aromatic compound or alkyl-substituted heterocyclic compound contains a halogen atom at the aromatic ring or the heterocyclic ring.

9. The process of claim 1 wherein the catalyst component (a) is at least one composite oxide selected from the group consisting of a binary composite oxide $TiO_2$—$SiO_2$ composed of 20 to 95 mole % titania ($TiO_2$) and 5 to 80 mole % of silica ($SiO_2$), a binary composite oxide $TiO_2$—$ZrO_2$ composed of 20 to 95 mole % of $TiO_2$ and 5 to 80 mole % of zirconia ($ZrO_2$) and a ternary composite oxide $TiO_2$—$SiO_2$—$ZrO_2$ composed of 20 to 95 mole % of $TiO_2$ and 5 to 80 mole % of $SiO_2$ and $ZrO_2$ combined provided that the proportions of $SiO_2$ and $ZrO_2$ are not zero.

10. The process of claim 1 wherein the composite oxide as component (a) has a specific surface area of at least 30 m$^2$/g.

11. The process of claim 1 wherein the composite oxide as component (a) is obtained by calcining a precursor thereof at a temperature of 300° to 800° C., said precursor being at least one hydrous oxide compound selected from the group consisting of a binary hydrous oxide compound of titanium and silicon, a binary hydrous oxide compound of titanium and zirconium and a ternary hydrous oxide compound of titanium, silicon and zirconium.

12. The process of claim 11 wherein the composite oxide as component (a) is obtained by calcining said precursor thereof at a temperature of 400° to 600° C.

13. The process of claim 1 wherein the catalyst composition is composed of 50 to 99% by weight of the component (a) and 1 to 50% by weight of the component (b).

14. The process of claim 1 wherein the catalyst composition is composed of 80 to 93% by weight of the component (a) and 7 to 20% by weight of the component (b), and the component (b) is composed of 2 5% by weight, as $V_2O_5$, of an oxide of vanadium and 5 to 15% by weight, as $Sb_2O_3$, of an oxide of antimony.

15. The process of claim 1 wherein the catalyst composition is supported on an inert carrier.

16. The process of claim 15 wherein the inert carrier has a specific surface area of 0.05 to 10 m$^2$/g.

17. The process of claim 15 wherein the inert carrier is silicon carbide.

18. The process of claim 15 wherein the amount of the catalyst composition deposited on the inert carrier is at least 3% by weight.

19. The process of claim 18 wherein the amount of the catalyst composition deposited on the inert carrier is at least 7% by weight.

* * * * *

UNITED STATES PATENT AND TRADEMARK OFFICE
CERTIFICATE OF CORRECTION

PATENT NO. : 4,939,260
DATED : July 3, 1990
INVENTOR(S) : INOUE, ET AL.

It is certified that error appears in the above-identified patent and that said Letters Patent is hereby corrected as shown below:

Column 8,
Claim 1, line 65, after "reacting", insert --(i)--.

Column 9, line 3, after "with", insert --(ii)--; after "and", insert --(iii)--.

Column 10,
Claim 14, line 34, after "2", insert --to--.

Signed and Sealed this

Seventh Day of July, 1992

Attest:

DOUGLAS B. COMER

*Attesting Officer*  *Acting Commissioner of Patents and Trademarks*